United States Patent

Shahi et al.

[11] Patent Number: 5,178,880
[45] Date of Patent: Jan. 12, 1993

[54] LIQUID SUSPENSIONS OF NITROFURANTOIN

[75] Inventors: Vijay Shahi, New Bombay, India; Margaret A. McGowan, Oxford; Michael J. Kane, Norwich, both of N.Y.

[73] Assignee: Norwich Eaton Pharmaceuticals, Inc., Norwich, N.Y.

[21] Appl. No.: 385,646

[22] Filed: Jul. 25, 1989

[51] Int. Cl.$^5$ .................... A61K 31/415; A61K 9/10
[52] U.S. Cl. .................................. 424/489; 514/387
[58] Field of Search .................. 514/397; 424/489

[56] References Cited

U.S. PATENT DOCUMENTS

| | | | |
|---|---|---|---|
| 2,610,181 | 9/1952 | Hayes | 260/240 |
| 3,401,221 | 9/1968 | Borgmann et al. | 424/273 |
| 4,122,157 | 10/1978 | Huber | 424/19 |
| 4,191,772 | 3/1980 | Woog et al. | 424/273 R |
| 4,370,313 | 10/1983 | Davies | 424/476 |

FOREIGN PATENT DOCUMENTS 250023 12/1987 European Pat. Off. .
250038 12/1987 European Pat. Off. .

OTHER PUBLICATIONS

The Merck Index, 11th Ed. (Rahway, N.J. Merck & Co., 1989) p. 9010 No. 9011.
H. Seager, "The effect of methylcellulose on the absorption of nitrofurantoin from the gastrointestinal tract," 20 J. Pharm. Pharmacol. 968 (1968).
I. McGilveray et al., "A study of bioavailabilities and dissolution rates of commercial tablets of nitrofurantoin," 23 J. Pharm. Pharmacol. 246S (1971).
M. Soci et al., "Influence of Viscosity on Absorption from Nitrofurantoin Suspensions," 69 J. Pharmaceutical Sciences 403 (1980).
"Nitrofurantoin", Martindale—The Extra Pharmacopoeia, 28th ed. 1049 (1982).
H. Paul et al., "Laboratory Studies with Nitrofurantoin", 56 J. Pharmaceutical Sciences 882 (1967).
N. Shah et al., "Effect of Polymers on Dissolution from Drug Suspensions", 65 J. Pharmaceutical Sciences 1618 (1976).
A. S. Geneidi et al., "Solid Dispersions of Nitrofurantoin, Ethotoin, and Coumarin with Polyethylene Glycol 6000 and Their Coprecipitates with Povidone 25,000", 67 J. Pharmaceutical Sciences 114 (1976).
M. A. El Egakey, "In vitro and in vivo Release Studies of Nitrofurantoin from Coated Crystals", 28 Acta Pharm. Technol. 267 (1982).

Primary Examiner—Robert T. Bond
Assistant Examiner—E. C. Ward
Attorney, Agent, or Firm—David L. Suter; Karen F. Clark; Jack D. Schaeffer

[57] ABSTRACT

Compositions, for the administration of nitrofurantoin to a human or other animal subject, comprising:
(a) a safe and effective amount of nitrofurantoin particulates having a surface consisting of nitrofurantoin monohydrate, wherein said particulates have a mean particle size greater than about 200 mesh size;
(b) nitrofurantoin monohydrate;
(c) an effective amount of a suspending agent; and
(d) water;
wherein the pH of said composition is from about 1 to about 6; and said nitrofurantoin monohydrate is dissolved in said water at saturation level. The nitrofurantoin of this invention are highly efficacious for the oral delivery of nitrofurantoin.

11 Claims, 2 Drawing Sheets

LIQUID SUSPENSIONS OF NITROFURANTOIN

BACKGROUND OF THE INVENTION

This invention relates to compositions useful as antibacterial agents in humans and other animals. In particular, it relates to liquid suspensions containing macrocrystalline nitrofurantoin.

Nitrofurantoin is an antibacterial agent used extensively in the treatment of urinary tract infections. It is rapidly absorbed in the gastrointestinal tract, and reaches high concentrations in the urine. A general description of nitrofurantoin is found in D. E. Cadwallader, 15 *J. American Pharmaceutical Association* 409 (1975); and J. D. Conklin, "The Pharmacokinetics of Nitrofurantoin and Its Related Bioavailability," 25 *Antibiotics and Chemotherapy* 233 (1978).

As with many other pharmaceutical active materials, the pharmacokinetics of nitrofurantoin may be affected by the size and type of nitrofurantoin crystals used in a dosage form. See, for example, J. K. Haleblian, "Characterization of Habits and Crystalline Modification of Solids and Their Pharmaceutical Applications", 66 *J. Pharmaceutical Sciences* 1269 (1975). In particular, the use of macrocrystalline nitrofurantoin has been found to reduce the level of emetic side effects that may be associated with nitrofurantoin. This association is discussed in the following articles: H. E. Paul et al., "Laboratory Studies with Nitrofurantoin", 56 *J. Pharmaceutical Sciences* 882 (1967), and N. Garti et al., "Habit Modifications of Nitrofurantoin Crystallized from Formic Acid Mixtures", 6 *Drug Development and Industrial Pharmacy* 379 (1980). Macrocrystalline nitrofurantoin having a surface area of from 120 cm$^2$/g (0.012M$^2$/g) to 1000 cm$^2$/g (0.1M$^2$/g) is described in U.S. Pat. No. 3,401,221, Borgmann et al., issued Sep. 10, 1968.

Nitrofurantoin is marketed by Norwich Eaton Pharmaceuticals, Inc., in several dosage forms using nitrofurantoin of differing crystal size. One such dosage form is a suspension of nitrofurantoin monohydrate. The crystals of nitrofurantoin in these suspensions are fine particles typically smaller than 170 mesh. Another solid dosage form contains relatively large crystals of anhydrous nitrofurantoin (from about 40 to about 200 mesh), in a capsule (marketed under the tradename "Macrodantin"). The BET surface area of these macrocrystals is from about 0.06M$^2$/g to about 0.15M$^2$/g.

A variety of dosage forms of nitrofurantoin are also known in the pharmaceutical literature. For example, solid oral dosage forms of nitrofurantoin are described in U.S. Pat. No. 4,122,157, Huber, issued Oct. 24, 1978; U.S. Pat. No. 4,370,313, Davies, issued Jan. 25, 1983; European Patent Publication 250,023, Patel et al., published Dec. 23, 1987; and European Patent Publication 250,038, Patel, published Dec. 23, 1987. Suspensions of nitrofurantoin are described in N. Shah et al., "Effect of Polymers on Dissolution from Drug Suspensions", 65 *J. Pharmaceutical Sciences* 1618 (1976).

None of these references, however, describes an aqueous suspension of macrocrystalline nitrofurantoin. Such a suspension would combine the highly desirable pharmacokinetics of commercially available macrocrystalline nitrofurantoin capsules (Macrodantin), with the benefits of pharmaceutical suspensions. Suspensions may be desirable, for example, for treatment of patients who are unable to swallow capsule or tablet dosage forms. Also, suspensions may facilitate treatment of gastrointestinal disorders, providing rapid and even dispersion of the pharmaceutical active in gastric fluids.

SUMMARY OF THE INVENTION

The present invention provides compositions, for the administration of nitrofurantoin to a human or other animal subject, comprising:
(a) a safe and effective amount of nitrofurantoin particulates having a surface consisting of nitrofurantoin monohydrate, wherein said particulates have a mean particle size greater than about 200 mesh size;
(b) nitrofurantoin monohydrate;
(c) an effective amount of a suspending agent; and
(d) water;
wherein the pH of said composition is from about 1 to about 6; and said nitrofurantoin monohydrate is dissolved in said water at saturation level.

The compositions of this invention are highly efficacious for the oral delivery of nitrofurantoin. In particular, this invention provides stable, efficacious, aqueous nitrofurantoin suspensions, for the treatment of gastrointestinal disorders and urinary tract infections, without undue side effects.

DESCRIPTION OF THE DRAWINGS

The attached drawings are photomicrographs of different particulate forms of nitrofurantoin. Specifically.

These photomicrographs were obtained by mounting the particulates on a Cambridge-type pin stub with double stick tape. (Sectional views were obtained by fracturing the particulates using gentle pressure from a glass coverslip.) The particulates, after mounting, were coated with 200A gold-palladium in a Balzers SCD 040 sputter coater. Examination of the crystals was in a JEOL 840 II scanning electron microscope operated at 20 KV (kilovolts). Images were recorded on a Polaroid P/N 55 film at a magnification of 100 for FIGS. 1–3, and 300 for FIG. 4.

DESCRIPTION OF THE INVENTION

The present invention encompasses certain novel nitrofurantoin dosage forms, useful for administering nitrofurantoin to a human or other animal subject. Specific compounds and compositions to be used in this invention must, accordingly, be pharmaceutically acceptable. As used herein, such a "pharmaceutically-acceptable" component is one that is suitable for use with humans/and or animals without undue adverse side effects (such as toxicity, irritation, and allergic response) commensurate with a reasonable benefit/risk ratio.

The compositions of this invention contain four essential components: nitrofurantoin particulates, nitrofurantoin monohydrate, a suspending agent and water. In particular, these compositions comprise:

(a) a safe and effective amount of nitrofurantoin particulates having a surface consisting of nitrofurantoin monohydrate, wherein said particulates have a mean particle size greater than about 200 mesh size;
(b) nitrofurantoin monohydrate;
(c) an effective amount of a suspending agent; and
(d) water;
wherein the pH of said composition is from about 1 to about 6; and said nitrofurantoin monohydrate is dissolved in said water at saturation level.

Preferably, the nitrofurantoin particulates are present at a level of from about 0.1% to about 3.5%, more preferably from about 0.1% to about 1.0%, more preferably from about 0.2% to about 0.6%. (Unless specified otherwise, all percentages are by total weight of composition.) Also preferably, the pH of the composition is from about 2.6 to about 6, more preferably from about 3.0 to about 5.5, more preferably from about 3.5 to about 5.0.

Figure 1:
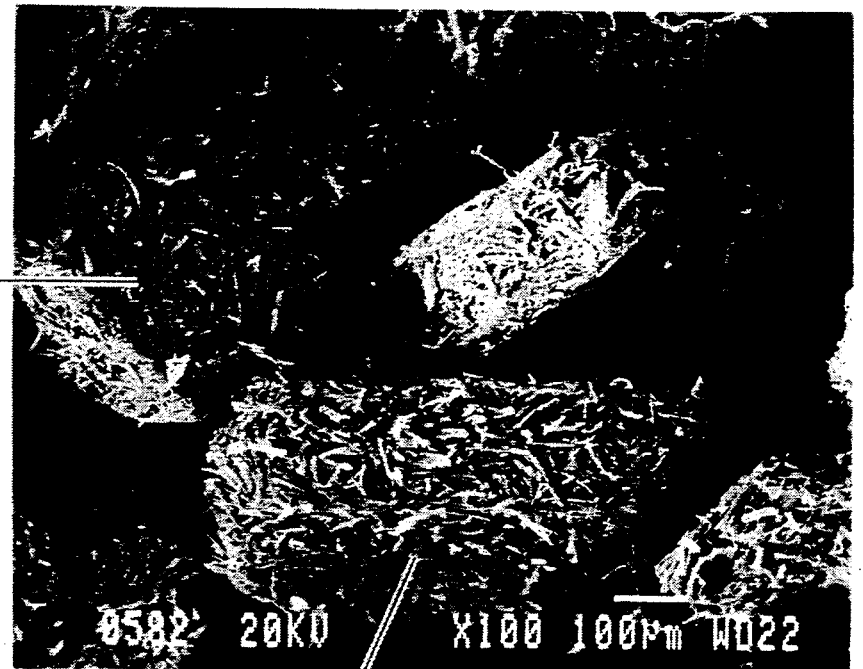
FIG. 1 depicts a perspective view of several nitrofurantoin particulates useful in the compositions of this invention.
Figure 2:
FIG. 2 depicts a perspective view of several particles of macrocrystalline nitrofurantoin.
Figure 3:
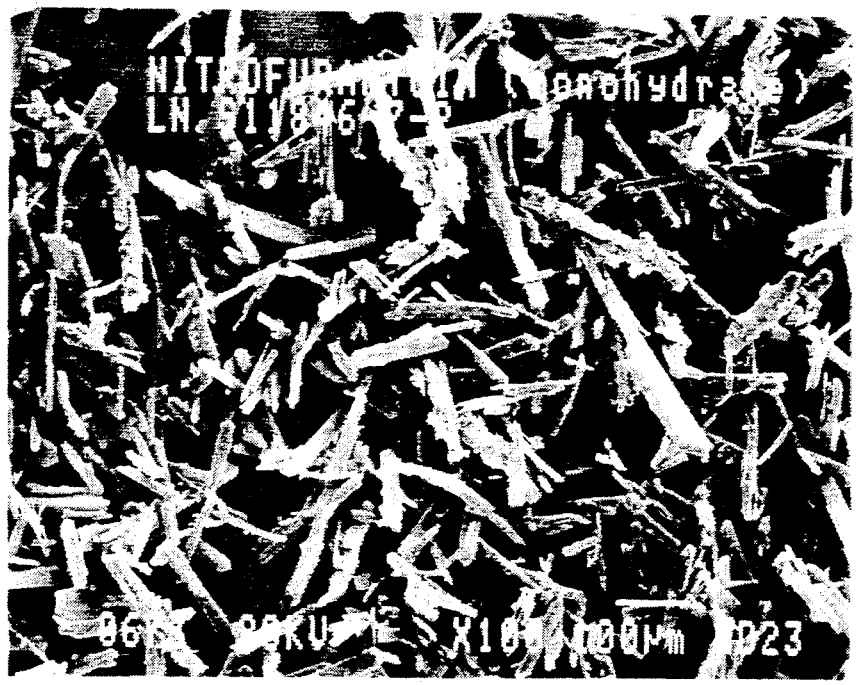
FIG. 3 depicts a perspective view of several particles of nitrofurantoin monohydrate.
Figure 4:
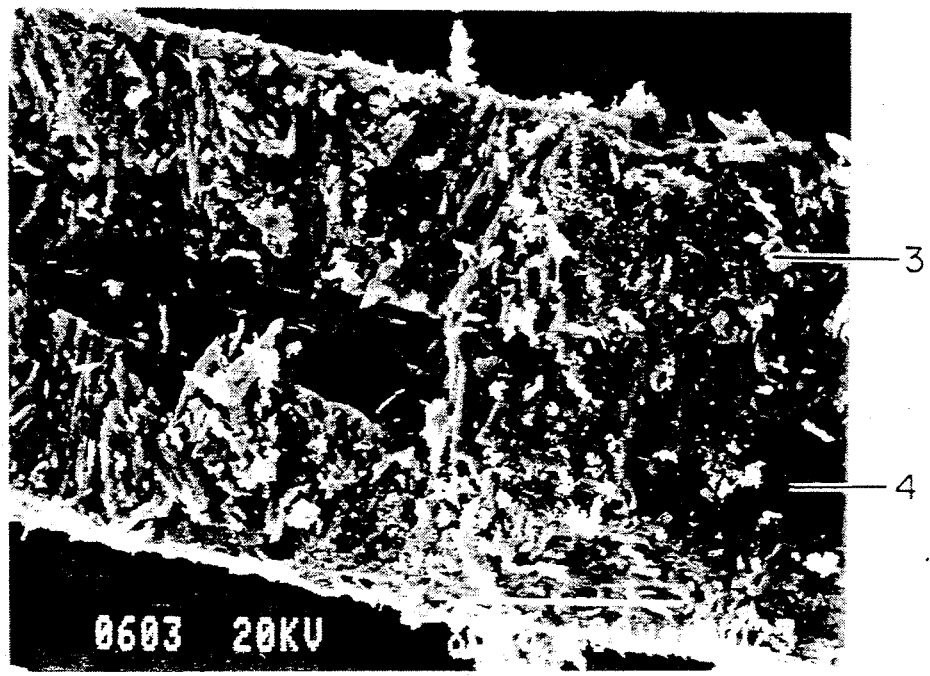
FIG. 4 is a longitudinal sectional view of a portion of a nitrofurantoin particulate useful in the compositions of this invention, comprising approximately 98% nitrofurantoin monohydrate; A more detailed description of the drawings is set forth in the "Nitrofurantoin" subsection of the Description of the Invention, below.

Nitrofurantoin particulates and nitrofurantoin monohydrate:

"Nitrofurantoin" includes 1-[[(5-nitro-2-furanyl)methylene]-amino]-2,2-imidazolidinedione, and related compounds described in U.S. Pat. No. 2,610,181, Hayes, issued Sep. 9, 1952 (incorporated by reference herein). Nitrofurantoin is described in the U.S. Pharmacopeia XXI (incorporated by reference herein). Nitrofurantoin may be made in a variety of physical forms, including (for example) "nitrofurantoin monohydrate" which contains about one mole of water chemically associated with one mole of nitrofurantoin. Nitrofurantoin monohydrate typically occurs in small, needlelike prisms. The crystals are transparent yellow with an adamantine luster. Such crystals are seen in FIG. 3 of the drawings. In contrast, "anhydrous nitrofurantoin" contains essentially no chemically-bonded water, and typically occurs in pinacoid prisms with a length:width ratio of about 3:1. The crystals are transparent to translucent yellow, with a nonmetallic waxy luster. Such crystals are seen in FIG. 2 of the drawings. (Descriptive terms for crystals and particulates, used herein, are discussed in B. Mason and L. Berry, *Elements of Mineralogy* (1969), incorporated by reference herein.)

The compositions of this invention contain nitrofurantoin monohydrate "dissolved in said water saturation level", i.e., in solution at the maximum concentration of nitrofurantoin monohydrate possible in the aqueous composition, at ambient conditions. Therefore, the exact amount of nitrofurantoin monohydrate in the present compositions will depend upon the amount of water present, and the pH of the composition. For typical compositions, though, this level is from about 0.01% to about 0.027%. In preferred compositions, nitrofurantoin monohydrate is present at a level of from about 0.01% to about 0.018%.

The "nitrofurantoin particulates" of this invention are comprised of discrete particulates of nitrofurantoin, having a surface consisting of nitrofurantoin monohydrate, wherein said particulates are larger than about 200 mesh size. Preferably the particulates have a size distribution of from about 30 mesh to about 100 mesh, more preferably from about 40 mesh to about 60 mesh. Also preferably, the BET surface area of the particulates is at least about $0.2 M^2/g$, more preferably at least about $0.4 M^2/g$. Preferred nitrofurantoin particulates useful herein are described in U.S. patent application Ser. No. 07/384,050 (Norwich Case N-537), Cazer et al., entitled "Nitrofurantoin Crystals", filed Jul. 25, 1989, incorporated by reference herein.

In the commercial manufacture of nitrofurantoin particulates useful in this invention, the particle size and BET surface area of the particulates may vary somewhat from the ranges described herein. Such commercial materials may have a distribution of values for these parameters, with mean values within the ranges described above.

A "safe and effective amount" of nitrofurantoin particulates is an amount that is effective to inhibit microbial growth at the site of an infection to be treated in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the nitrofurantoin particulates therein, and the dosage regimen desired for the composition.

As referred to herein, "size" of the nitrofurantoin particulates of this invention refers to the measurement of the largest U. S. Standard mesh screen through which substantially all of the particulates will pass. In general, this mesh measurement is a function of the smallest dimension of the particulates being measured. As this minimum dimension of the particulates increases, the mesh size will decrease. For example, as used herein, particulates "larger than about 200 mesh size" means that substantially all of the particulates will pass through a U. S. Standard mesh screen of less than 200 mesh, with few particulates passing through the 200 mesh screen. Also, particulates having a size distribution "of from about 40 mesh to about 60 mesh" (also referred to as "40/60 mesh" particles) means that substantially all of the particulates will pass through a 40 mesh screen, and essentially none of the particles will pass through a 60 mesh screen. Mesh measurements are discussed in "Screening", *Chemical Engineer's Handbook*, 4th Edition 21-46 (J. Perry, editor), incorporated by reference herein.

As referred to herein, "the BET surface area" of nitrofurantoin particulates refers to the measurement of the surface area in immediate contact with an inert gas into which the particulate is placed, measured by the means generally described in S. Brunnaer et al., *60 J. American Chemical Society* 309A (1938), incorporated by reference herein, using a single point measurement technique on a Micromeritics Flowsorb II 2300 (manufactured by Micromeritics Instrument Corporation, Norcross, Ga., U.S.A.). The particulate sample is degassed at approximately 140° C. (284° F.) for approximately 15 minutes. The analysis gas is nitrogen/helium at a molar ratio of 30/70. Cooling baths are liquid nitrogen, and the apparatus is calibrated using nitrogen gas injected with a gas-tight syringe.

Preferred nitrofurantoin particulates useful in this invention have bulk physical characteristics similar to those of macrocrystalline anhydrous nitrofurantoin. In particular, the nitrofurantoin particulates are typically pinacoid prisms with a length:width ratio of about 3:1. These particulates are acicular microcrystalline aggregates with a nonmetallic silky to earthy luster. Several of these nitrofurantoin particulates are depicted in FIG.

1. Particulate 1 is a perspective view, showing both a face along its long axis and a face along its short axis. Particulate 2 is a perspective view, showing two faces along the long axis of the particulate. The similarity of the bulk physical characteristics of these particulates to the bulk physical characteristics of macrocrystalline anhydrous nitrofurantoin can be seen by comparison of the particulates depicted in FIG. 1 with those depicted in FIG. 2.

The surface of the nitrofurantoin particulates preferably consists essentially of nitrofurantoin monohydrate. The "surface" is the portion of the nitrofurantoin particulate that is in immediate contact with a fluid into which the particulate is submersed. The remaining, inner portion of the nitrofurantoin particulate (the "core") is comprised of anhydrous nitrofurantoin, nitrofurantoin monohydrate, or mixtures thereof.

Accordingly, the nitrofurantoin particulates of this invention are preferably comprised of from about 5% to about 100% of nitrofurantoin monohydrate. More preferably, the nitrofurantoin particulates comprise at least about 50%, more preferably at least about 90%, nitrofurantoin monohydrate. Nitrofurantoin particulates containing less than 100% nitrofurantoin monohydrate consist of: a "surface layer" comprising nitrofurantoin monohydrate as the monohydrate crystalline forms on the surface, and in the contiguous portion of the core; with the remaining portion (if any) of the core comprising anhydrous nitrofurantoin.

The portion of nitrofurantoin particulates comprised by nitrofurantoin monohydrate and nitrofurantoin anhydrous may be determined using standard analytical techniques well know in the art. In particular, the relative proportion of nitrofurantoin monohydrate in the nitrofurantoin particulates may be determined by thermogravimetric analysis. The chemically-bonded water of the monohydrate is driven off by heating, resulting in a weight loss. This weight loss is a function of the amount of monohydrate in a sample analyzed. Specifically, a thermogravimetric scan is performed on a sample of nitrofurantoin particulates (unground) of from about 5 to about 10 milligrams, under nitrogen, over the temperature range of from about 30° C. (86° F.) to about 220° C. (428° F.), scanned at a rate of about 5° C. per minute. The chemically-bound water is measured as the weight loss occurring in the range of from about 80° C. (176° F.) to about 150° C. (302° F.). This lost weight constitutes approximately 7% of the weight of the nitrofurantoin monohydrate originally in the sample. Accordingly, the weight of nitrofurantoin monohydrate in the sample is determined by multiplying the weight of lost water by approximately 14.3. This weight is then compared to the weight of the original sample, to determine the percentage of nitrofurantoin monohydrate in the sample. A general description of such analyses useful herein is set forth in *Thermal Analysis*, 3d edition (W. Wendlandt, editor, 1986), incorporated by reference herein.

The presence of nitrofurantoin monohydrate on the surface of the particulates may be determined by attenuated total reflectance infrared spectroscopy. Samples of particulates are placed on a KRS-5 crystal (having approximately 50 cm×3 cm×3 cm dimensions), at a 45 degree entry angle. A 4 cm$^{-1}$ resolution spectrum is obtained over the range of from about 4000 cm$^{-1}$ to about 450 cm$^{-1}$. Distinct absorbance is seen at the following wavenumbers (+/−5): 3618, 3474, 1778, 1723, 1132, 1018, 893, and 877. By comparison, absorbance for anhydrous nitrofurantoin is seen at the following wavenumbers (+/−5): 1800, 1775, 1741, 1724, 1104, 1013, 901, and 867. Anhydrous nitrofurantoin will also pass identity test part B for nitrofurantoin, U.S. Pharmacopeia XXI, page 735 (incorporated by reference herein).

Preferred nitrofurantoin particulates among those useful in this invention may be made by the method comprising the steps of:

(a) preparing a saturated aqueous solution of nitrofurantoin monohydrate;

(b) adding to said solution anhydrous nitrofurantoin having a particle size larger than about 200 mesh, at a level of about 100 grams per liter of said solution;

(c) mixing said solution for at least about 5 minutes; and (d) filtering said solution.

The anhydrous nitrofurantoin added in step (b) preferably has a particle size distribution of from about 30 mesh to about 100 mesh, more preferably from about 40 mesh to about 60 mesh. This particle size is selected to yield the particular particle size desired in the final nitrofurantoin particulate product. Preferably, said solution is mixed in step (c) for at least about 6.5 hours.

The anhydrous nitrofurantoin and the saturated nitrofurantoin monohydrate solution are mixed, in step (c), for a period of time sufficient to yield a particulate having a desired nitrofurantoin monohydrate composition. Nitrofurantoin particulates having low levels of nitrofurantoin monohydrate (i.e., about 5%) are prepared by processes wherein this mixing step is about 5 minutes. Nitrofurantoin particulates comprising about 100% nitrofurantoin monohydrate are made by processes wherein the mixing step is continued for about 24 hours. The specific duration of the mixing step will vary according to such factors as the size and configuration of the mixing vessel, the rate of mixing, and the size and surface characteristics of the nitrofurantoin anhydrous crystals used (the effective surface area of nitrofurantoin anhydrous exposed to the saturated solution of nitrofurantoin monohydrate). The specific mixing time to yield a nitrofurantoin particulate having a specific composition of nitrofurantoin monohydrate may be determined by routine experimentation.

Suspension Agent

The compositions of this invention employ a suspension system comprising one or more compounds (herein "a suspension agent") that maintain the nitrofurantoin particulates in an essentially uniform aqueous suspension at typical conditions of storage and use. Such suspension systems, suspension agents, and methods of their use include those well known in the art. See, for example, M. Pernarowski, "Solutions, Emulsions and Suspensions", *Remington's Pharmaceutical Sciences* (A. Osol, editor, 15th Edition, 1975), incorporated by reference herein. Suspension agents useful in the compositions of this invention include, for example, cellulose ethers (such as methylcellulose, hydroxyethylcellulose, and carboxymethylcellulose), alginates, carboxyvinyl-polymers, xanthan gum, colloidal silicas, montmorillonite clays and hydrophobically treated montmorillonite clays (such as magnesium aluminum silicate), and mixtures thereof. Preferred suspension agents include mixtures of cellulose ethers and magnesium aluminum silicate.

One preferred suspension system employs a mixture of methylcellulose and magnesium aluminum silicate. In such a system, methylcellulose may be used at levels of from about 0.1% to about 10%, preferably from 0.5% to about 1.5%, and magnesium aluminum silicate may be used at levels of from about 0.19% to about 10%, preferably from about 2.5% to about 4.0%. Methylcellulose, or cellulose methyl ether, is commercially available from a variety of sources as a chemically treated plant cellulose derivative. Among such methylcellulose materials useful herein is Methocel, sold by Dow Chemical Company. Magnesium aluminum silicate (or aluminum magnesium silicate) is of the formula $Al_2MgO_8Si_2$, occurring naturally in such smectite minerals as colerainite, saponite, and sapphirine. Refined magnesium aluminum silicates useful herein are readily available, such as Veegum, manufactured by R. T. Vanderbilt Company, Inc.

Optional Components

The compositions of the present invention may also contain optional components that modify the physical characteristics and/or therapeutic effects of the compositions. Such optional components must not, however, substantially affect, in an adverse manner, the therapeutic activity of the nitrofurantoin particulates. The optional components useful herein must not also substantially affect, in an undesired manner, the viscosity of the aqueous suspension. Preferred optional components useful herein include colorants, sweeteners, and flavorants, typically at levels of from about 0.01% to about 0.2%. A dispersant material, such as glycerin, is a preferred optional angredient, present at a level of from about 5% to about 40%, preferably from about 10% to about 20%.

The compositions of this invention preferably contain an "antiseptic agent", i.e., one or more materials that prevent or arrest the growth or action of microorganisms by inhibiting their activity and/or by destroying them. These materials are preferably present at a level of from about 0.001% to about 0.5%. Many antiseptic materials are known in the art, including preservatives, disinfectants and antiseptics. Such materials are described, for example, in *Disinfection, Sterilization and Preservation* 3d (S. Block ed., 1983), incorporated by reference herein.

The pH of the present compositions may be adjusted by addition of a pharmaceutically-acceptable acid or base. Suitable acids include, for example, hydrochloric acid and carboxylic acids such as citric acid, tartaric acid and succinic acid. Suitable bases include, for example, the oxides and hydroxides of calcium, potassium, sodium and magnesium, alkaline quaternary compounds, alkaline amino acids, and mixtures thereof.

The compositions of this invention may be made by any of a variety of processes well known in the industry. Such processes typically involve admixture of the components, followed by homogenizing. As will be appreciated by those skilled in the art, the conditions under which the compositions are mixed and homogenized may have an effect on the product viscosity.

Methods of Administration

This invention also provides methods of treating or preventing an infectious disorder in a human or other animal subject, by administering a safe and effective amount of a nitrofurantoin suspension of this invention, to said subject. As used herein, an "infectious disorder" is any disorder characterized by the presence of a microbial infection. Preferred methods of this invention are for the treatment of bacterial infections, particularly for genitourinary infections, and gastrointestinal infections.

The specific dosage of nitrofurantoin to be administered, as well as the duration of treatment, are mutually dependent. The dosage and treatment regimen will also depend upon such factors as the type of dosage form used, the infectious agent present, the ability of the nitrofurantoin particulates to reach sustained effective levels at the site of the infection, the nature and extent of other infections (if any), the personal attributes of the subject (such as weight), compliance with the treatment regimen, and the presence and severity of any side effects of the treatment.

Typically, for a human adult (weighing approximately 70 kilograms), from about 1 mg to about 1,000 mg, more preferably from about 10 mg to about 400 mg, more preferably from about 20 mg to about 200 mg, of nitrofurantoin particulates are administered per day. Treatment regimens preferably extend from about 3 to about 56 days, preferably from about 7 to about 28 days, in duration.

Preferred methods of this invention include methods for the treatment and prophylaxis of upper-gastrointestinal disorders mediated by *Campylobacter pylori*. Such methods are generally described in European Patent Publication 219,912, Kraft et al., published Apr. 29, 1987, incorporated by reference herein. Preferred methods for the treatment of a human or other animal subject having such upper-gastrointestinal disorders comprise administering to said subject nitrofurantoin particulates at a level of from about 10 mg to about 400 mg per day, for from about 3 to about 60 days.

EXAMPLE I

Nitrofurantoin particulates for use in this invention are made by adding approximately 200 g (grams) of nitrofurantoin monohydrate to approximately 40 L (liters) of deionized water, in a suitable container. This mixture is stirred for approximately 30 minutes, at ambient temperature (approximately 68° F., 20° C.). The mixture is then filtered, removing the undissolved nitrofurantoin monohydrate.

Approximately 4 kg (kilograms) of 40/60 mesh screened anhydrous nitrofurantoin macrocrystals are then added to the saturated nitrofurantoin monohydrate solution. This mixture is then stirred for approximately 6.5 hours, at ambient temperature.

The mixture is then filtered, and the nitrofurantoin particulates washed with ether. The particulates are then air dried for approximately 1 hour. The particulates are further dried for approximately 24 hours at 60° C. (140° F.).

Thermal gravimetric analysis of the particulates indicates that the particulates are comprised of approximately 98% nitrofurantoin monohydrate. The particles are screened, and are found to have a size of from 40 to 60 mesh. The BET surface area is measured to be approximately $5.8 M^2/g$. An attenuated reflectance infrared spectrum is performed, and distinct absorbance is seen at the wavenumbers characteristic of nitrofurantoin monohydrate.

A composition of this invention is then made having the following composition:

| Component | % (by weight) |
|---|---|
| nitrofurantoin particulates | 0.508 |
| nitrofurantoin monohydrate | 0.018 |

-continued

| Component | % (by weight) |
| --- | --- |
| magnesium aluminum silicate | 3.010 |
| sodium carboxymethylcellulose | 1.180 |
| glycerin | 13.570 |
| sorbitol | 15.050 |
| methyl paraben | 0.129 |
| propyl paraben | 0.022 |
| citric acid | 0.726 |
| purified water | 65.787 |

The magnesium aluminum silicate is added to approximately one third of the water, and mixed for approximately one hour, at approximately 50° C. (122° F.). Separately, the glycerin, methyl paraben, propyl paraben, and carboxymethylcellulose are mixed. This mixture is then slowly added to the magnesium aluminum silicate/water mixture. The sorbitol, citric acid and remaining water is added, and the mixture stirred for approximately 1.5 hours.

The nitrofurantoin monohydrate is then added to the solution, and mixed for approximately 2 hours. The nitrofurantoin particulates are added, and the mixture stirred for approximately 3 hours.

A human subject suffering from gastritis mediated by *Campylobacter pylori* is administered approximately 20 ml of this suspension (approximately 100 mg of nitrofurantoin), 4 times a day, for 28 days. Stomach cultures of the subject indicate the organism has been eradicted, with corresponding improvement in the subject's symptoms.

EXAMPLE II

A composition according to this invention is made comprised as follows.

| Component | % (by weight) |
| --- | --- |
| nitrofurantoin particulates* | 0.53 |
| nitrofurantoin monohydrate | 0.02 |
| magnesium aluminum silicate | 1.20 |
| pectin | 1.11 |
| glycerin | 20.18 |
| methyl paraben | 0.12 |
| propyl paraben | 0.02 |
| purified water | 76.82 |

*made according to the method described in Example I

The composition is made by dissolving the methyl paraben and propyl paraben in a portion of the water, followed by the magnesium aluminum silicate, to form a "bulk mixture". The bulk mixture is then stirred for approximately 1 hour. The pectin is then added to approximately one-half of the glycerin, mixed for approximately 1 hour, and added to the bulk mixture. The nitrofurantoin monohydrate is then added. Separately, the nitrofurantoin particulates are added to the remaining portion of glycerin. This mixture is finally added to the bulk mixture, and the final composition stirred for approximately 1 hour.

A human subject suffering from a urinary tract infection caused by *Escherichia coli* is administered approximately 20 ml of this suspension (approximately 100 mg of nitrofurantoin), 4 times a day, for 10 days. The infection is thereby eradicated.

EXAMPLE III

A composition according to this invention is made comprised as follows:

| Component | % (by weight) |
| --- | --- |
| nitrofurantoin particulates* | 1.000 |
| nitrofurantoin monohydrate | 0.025 |
| magnesium aluminum silicate | 0.500 |
| xanthan gum | 0.600 |
| flavorants | 0.080 |
| methyl paraben | 0.120 |
| propyl paraben | 0.020 |
| purified water | 97.655 |

*made according to the method described in Example 1

The composition is made by dissolving the methyl paraben, propyl paraben, and flavorants in a portion of the water, followed by the magnesium aluminum silicate, to form a "bulk mixture". The bulk mixture is then stirred for approximately 1 hour. The xanthan gum then added to the bulk mixture, and stirred for approximately 20 minutes. The nitrofurantoin monohydrate is then added. The nitrofurantoin particulates are then added, and the final composition stirred for approximately 1 hour.

A human subject suffering from a urinary tract infection is administered approximately 20 ml of this suspension (approximately 200 mg of nitrofurantoin), 2 times a day, for 10 days. The infection is thereby eradicated.

What is claimed is:

1. A pharmaceutical suspension, for the administration of nitrofurantoin to a human or other animal subject, comprising:
   (a) from about 0.1% to about 3.5% of nitrofurantoin particulates having a surface consisting of nitrofurantoin monohydrate, wherein said particulates have a mean particle size greater than about 200 mesh size;
   (b) from about 0.010% to about 0.027% of nitrofurantoin monohydrate;
   (c) an effective amount of a suspending agent; and
   (d) water;

wherein the pH of said composition is from about 1 to about 6; and said nitrofurantoin monohydrate is dissolved in said water at saturation level.

2. A composition, for the administration of nitrofurantoin to a human or other animal subject, according to claim 1, wherein said pH is from about 3.5 to about 5.0.

3. A composition, for the administration of nitrofurantoin to a human or other animal subject, according to claim 1, wherein said nitrofurantoin particulates have a BET surface area of at least about 0.2 $M^2/g$.

4. A composition, for the administration of nitrofurantoin to a human or other animal subject, according to claim 3, wherein said nitrofurantoin particulates have a size distribution of from about 40 mesh to about 60 mesh.

5. A composition, for the administration of nitrofurantoin to a human or other animal subject, according to claim 4, wherein said nitrofurantoin particulates are made by a process comprising the steps of:
   (a) preparing a saturated aqueous solution of nitrofurantoin monohydrate;
   (b) adding to said solution anhydrous nitrofurantoin having a particle size larger than about 200 mesh;
   (c) mixing said solution for at least about 5 minutes; and
   (d) filtering said solution.

6. A composition, for the administration of nitrofurantoin to a human or other animal subject, according to claim 5, wherein said solution is mixed in said step (c) for at least about 6.5 hours.

7. A composition, for the administration of nitrofurantoin to a human or other animal subject, according to claim 4, wherein said suspension agent comprises methyl cellulose and magnesium aluminum silicate.

8. A composition, for the administration of nitrofurantoin to a human or other animal subject, according to claim 7, wherein said methyl cellulose is present at a level of from about 0.5% to about 1.5%, and said magnesium aluminum silicate is present at a level of from about 2.5% to about 4%.

9. A composition, for the administration of nitrofurantoin to a human or other animal subject, comprising:
 (a) from about 0.1% to about 3.5% of nitrofurantoin particulates having a surface consisting of nitrofurantoin monohydrate, wherein said particulates have a mean particle size distribution of from about 30 mesh to about 100 mesh and a BET surface area of at least about 0.2 $M^2/g$;
 (b) nitrofurantoin monohydrate;
 (c) methyl cellulose at a level of from about 0.1% to about 10%;
 (d) magnesium aluminum silicate a level of from about 0.2% to about 10%; and
 (e) water;
wherein the pH of said composition is from about 3 to about 5.5; and said nitrofurantoin monohydrate is dissolved in said water at saturation level.

10. A composition, for the administration of nitrofurantoin to a human or other animal subject, according to claim 9, wherein said nitrofurantoin particulates are present at a level of from about 0.2% to about 0.6%, and said BET surface area is at least about 0.4 $M^2/g$.

11. A composition, for the administration of nitrofurantoin to a human or other animal subject, according to claim 10, wherein said methyl cellulose is present at a level of from about 0.5% to about 1.5%, and said magnesium aluminum silicate is present at a level of from about 2.5% to about 4%.

* * * * *